United States Patent
Olejnik et al.

(10) Patent No.: US 10,337,050 B2
(45) Date of Patent: Jul. 2, 2019

(54) POLYPHENOLIC ADDITIVES IN SEQUENCING BY SYNTHESIS

(71) Applicant: QIAGEN Waltham, Inc., Waltham, MA (US)

(72) Inventors: Jerzy Olejnik, Brookline, MA (US); Michel Georges Perbost, Belmont, MA (US)

(73) Assignee: Qiagen Sciences, LLC, Germantown, MD (US)

(*) Notice: Subject to any disclaimer, the term of this patent is extended or adjusted under 35 U.S.C. 154(b) by 62 days.

(21) Appl. No.: 15/427,664

(22) Filed: Feb. 8, 2017

(65) Prior Publication Data

US 2017/0233796 A1  Aug. 17, 2017

Related U.S. Application Data

(60) Provisional application No. 62/419,685, filed on Nov. 9, 2016, provisional application No. 62/293,969, filed on Feb. 11, 2016.

(51) Int. Cl.
*C12Q 1/6823* (2018.01)
*C12Q 1/6869* (2018.01)
*C07H 21/02* (2006.01)

(52) U.S. Cl.
CPC .......... *C12Q 1/6823* (2013.01); *C12Q 1/6869* (2013.01)

(58) Field of Classification Search
CPC ............. C12Q 1/6869; C12Q 2527/125; C12Q 2535/113; C12Q 1/6823
See application file for complete search history.

(56) References Cited

U.S. PATENT DOCUMENTS

| | | | |
|---|---|---|---|
| 3,817,837 A | 6/1974 | Rubenstein et al. | 435/7.9 |
| 3,850,752 A | 11/1974 | Schuurs et al. | 435/7.93 |
| 3,939,350 A | 2/1976 | Kronick et al. | 250/365 |
| 3,996,345 A | 12/1976 | Ullman et al. | 436/537 |
| 4,275,149 A | 6/1981 | Litman et al. | 435/7.91 |
| 4,277,437 A | 7/1981 | Maggio | 422/401 |
| 4,366,241 A | 12/1982 | Tom et al. | 435/7.91 |
| 4,683,195 A | 7/1987 | Mullis et al. | 435/6.11 |
| 4,683,202 A | 7/1987 | Mullis | 435/91.2 |
| 5,116,734 A * | 5/1992 | Higgs | C12Q 1/26 435/28 |
| 6,187,286 B1 * | 2/2001 | Elmaleh | A61K 51/0491 424/1.11 |
| 6,664,079 B2 | 12/2003 | Ju et al. | 435/91.1 |
| 8,623,598 B2 | 1/2014 | Olejnik et al. | 435/6.1 |
| 9,145,589 B2 | 9/2015 | Gordon et al. | 435/6.1 |
| 2014/0234832 A1 * | 8/2014 | Olejnik et al. | 435/6.1 |

FOREIGN PATENT DOCUMENTS

JP  2004210741 A * 7/2004 ............. A61K 45/00

OTHER PUBLICATIONS

Bendary et al. (2013) Annals of Agricultural Science vol. 58(2) 173-181. (Year: 2013).*
JP2004210471—English translation (Year: 2004).*
Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.
Crumpton, J. B. et al. (2011) "Facile Analysis and Sequencing of Linear and Branched Peptide Boronic Acids by MALDI Mass Spectrometry," *Analytical Chemistry* 83(9), 3548-3554.
Dewick, P. M. et al. (1969) "Phenol biosynthesis in higher plants. Gallic acid," *Biochemical Journal* 113(3), 537-542.
Dieffenbach, C. W. et al. (1995) *PCR Primer, A Laboratory Manual*, Cold Spring Harbor Laboratory Press, Plainview, N.Y.
Fiuza, S. M. et al. (2004) "Phenolic acid derivatives with potential anticancer properties—a structure-activity relationship study. Part 1: Methyl, propyl and octyl esters of caffeic and gallic acids," *Bioorganic & Medicinal Chemistry* 12(13), 3581-3589.
Nakai, S. et al. (2000) "Myriophyllum spicatum-released allelopathic polyphenols inhibiting growth of blue-green algae Microcystis aeruginosa," *Water Research* 34(11), 3026-3032.
Schock, R. U. et al. (1951) "The Persulfate Oxidation of Salicylic Acid. 2,3,5-Trihydroxybenzoic Acid," *Journal of Organic Chemistry* 16(11), 1772-1775.
Strupat, K. et al. (1991) "2,5-Dihydroxybenzoic acid: a new matrix for laser desorption—ionization mass spectrometry," *International Journal of Mass Spectrometry and Ion Processes* 111(Supplement C), 89-102.
Wang, Z. et al. (2010) "Desulfurization of Cysteine—Containing Peptides Resulting from Sample Preparation for Protein Characterization by MS," *Rapid Communications in Mass Spectrometry* 24(3), 267-275.
Zucca, P. et al. (2013) "Evaluation of Antioxidant Potential of "Maltese Mushroom" (*Cynomorium coccineum*) by Means of Multiple Chemical and Biological Assays," *Nutrients* 5(1), 149-161.

* cited by examiner

*Primary Examiner* — Teresa E Strzelecka
(74) *Attorney, Agent, or Firm* — Medlen & Carroll, LLP

(57) ABSTRACT

The invention relates to methods, compositions, devices, systems and kits as described including, without limitation, reagents and mixtures for determining the identity of nucleic acids in nucleotide sequences using, for example, sequencing by synthesis methods. In particular, the present invention contemplates the use of polyphenolic compounds, known as antioxidant additives, to improve the efficiency of Sequencing-By-Synthesis reactions. For example, gallic acid (GA) is shown herein to be one of many exemplary SBS polyphenolic additives.

10 Claims, 12 Drawing Sheets

| Sample/Flowcell Number | Read Length Processed | Avg. Error Rate (%) | Avg. Percent Perfect | % Mapped | Lead | Lag | Filtered Error Rate (%) | Extrapolated Filtered Output (GB) |
|---|---|---|---|---|---|---|---|---|
| GR 5.17 Control | 106 | 2.82 | 35.58 | 29.89 | 0.28 | 0.21 | 0.6017 | 0.73 |
| GR 5.17 AddG | 106 | 1.72 | 57.98 | 30.66 | 0.18 | 0.18 | 0.4718 | 0.85 |
| GR 6.2 Control | 106 | 3.09 | 34.13 | 40.1 | 0.24 | 0.24 | 0.5168 | 0.88 |
| GR 6.2 AddG | 106 | 1.84 | 55.74 | 43.71 | 0.2 | 0.23 | 0.4912 | 1.23 |
| GR 6.20 Control | 106 | 2.65 | 35.44 | 41.17 | 0.27 | 0.25 | 0.5573 | 1 |
| GR 6.20 AddG | 106 | 1.97 | 54.53 | 43.12 | 0.22 | 0.27 | 0.5269 | 1.18 |
| GR 6.21 Control | 106 | 2.44 | 39.08 | 40.87 | 0.23 | 0.27 | 0.6064 | 1.13 |
| GR 6.21 AddG | 106 | 1.73 | 54.39 | 42.03 | 0.2 | 0.26 | 0.4511 | 1.15 |

Figure 1

| Baseline | | FP | TP |
|---|---|---|---|
| GR 5.17 Baseline | | 260 | 17 |
| GR 6.2 Baseline | | 403 | 20 |
| GR 6.20 Baseline | | 388 | 21 |
| GR 6.21 Baseline | | 329 | 21 |
| | | | |
| Additive G | | FP | TP |
| GR 5.17 Additive G | | 73 | 18 |
| GR 6.2 Additive G | | 85 | 20 |
| GR 6.20 Additive G | | 90 | 21 |
| GR 6.21 Additive G | | 82 | 21 |

Clones

| Sample/Flowcell Number | Read Length Processed | Avg. Error Rate (%) | Std. Error Rate (%) | Avg. Percent Perfect | Std. Percent Perfect | % Mapped | Extrapolated Throughput (GB) | Lead | Lag | Avg. Bead Retention (%) | Std. Bead Retention (%) |
|---|---|---|---|---|---|---|---|---|---|---|---|
| baseline 6.4 | 106 | 1.24 | 0.37 | 82.01 | 8.33 | 40.69 | 1.19 | 0.36 | 0.2 | 98 | 1 |
| Gentacid 6.4 | 106 | 1.17 | 0.24 | 73.64 | 3.33 | 39.26 | 1.16 | 0.3 | 0.25 | 96 | 2.5 |
| baseline 6.14 | 106 | 1.18 | 0.17 | 75.18 | 3.16 | 31.35 | 0.7 | 0.23 | 0.24 | 96 | 1 |
| PyroG 6.14 | 106 | 0.9 | 0.04 | 80.97 | 0.77 | 35.47 | 1.02 | 0.15 | 0.26 | 98 | 0.6 |
| baseline 6.15 | 106 | 2.01 | 0.25 | 49.12 | 4.46 | 31.28 | 0.71 | 0.45 | 0.18 | 97 | 1 |
| PyroC 6.15 | 106 | 1.34 | 0.29 | 73.38 | 2.75 | 35.56 | 1.03 | 0.2 | 0.28 | 98 | 0.3 |

Gene Panel

| Sample/Flowcell Number | Read Length Processed | Avg. Error Rate (%) | Std. Error Rate (%) | Avg. Percent Perfect | Std. Percent Perfect | % Mapped | Extrapolated Throughput (GB) | Lead | Lag | Avg. Bead Retention (%) | Std. Bead Retention (%) |
|---|---|---|---|---|---|---|---|---|---|---|---|
| baseline 6.4 | 100 | 2.24 | 0.34 | 42.42 | 5.96 | 41.17 | 1.34 | 0.31 | 0.2 | 98 | 0.2 |
| Gentacid 6.4 | 100 | 1.87 | 0.09 | 51.46 | 1.69 | 42.08 | 1.35 | 0.24 | 0.12 | 98 | 0.4 |
| baseline 6.14 | 100 | 2.65 | 0.55 | 39.13 | 4.3 | 43.11 | 1.36 | 0.26 | 0.23 | 97 | 0.3 |
| PyroG 6.14 | 100 | 1.61 | 0.32 | 57.43 | 3.34 | 45.73 | 1.47 | 0.19 | 0.24 | 99 | 0.4 |
| baseline 6.15 | 100 | 3.01 | 0.18 | 37.51 | 2.18 | 41.44 | 1.3 | 0.38 | 0.19 | 99 | 0.3 |
| PyroC 6.15 | 100 | 2.17 | 0.07 | 44.83 | 1.53 | 44.23 | 1.42 | 0.22 | 0.26 | 98 | 0.5 |

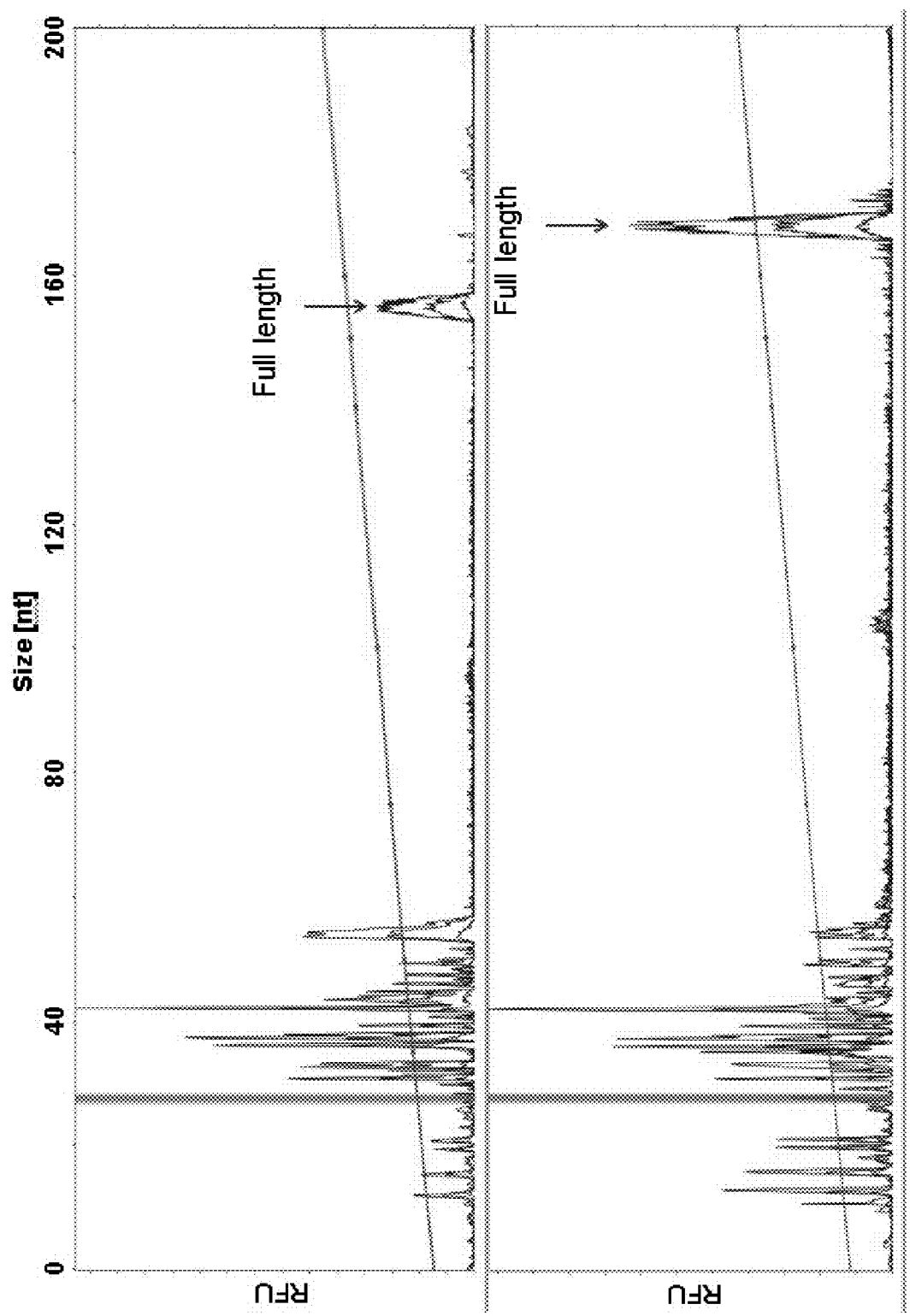

FIGURE 10

| Sample/Flowcell Number | Read Length Processed | # of Tiles Processed | Avg. Error Rate (%) | Std. Error Rate (%) | Avg. Percent Perfect | Std. Percent Perfect | Total Mapped Reads | Avg. Mapped Reads/Tile | Std. Mapped Reads/Tile | Total Perfect Reads | Avg. Perfect Reads/Tile | Std. Perfect Reads/Tile | Q27 | X Mapped | Throughput (GB) | Extrapolated Throughput (GB) |
|---|---|---|---|---|---|---|---|---|---|---|---|---|---|---|---|---|
| 5.4 fc1 | 100 | 60 | 1.13 | 0.13 | 67.38 | 5.73 | 53978646 | 886631 | 1244 | 34939461 | 568222 | 5078 | 10 | 22.99 | 0.52 | 0.65 |
| 5.4 fc2 | 100 | 60 | 1.12 | 0.11 | 68.1 | 4.35 | 50663925 | 843365 | 533 | 34447930 | 574686 | 3837 | 10 | 22.49 | 0.51 | 0.63 |
| 5.4 fc3 | 100 | 60 | 1.3 | 0.27 | 67.92 | 4.79 | 50338667 | 839978 | 734 | 34232272 | 570555 | 4255 | 10 | 22.5 | 0.5 | 0.63 |
| 5.4 fc4 | 100 | 60 | 1.21 | 0.35 | 66.95 | 5.17 | 49574219 | 826624 | 486 | 36183554 | 566893 | 4309 | 10 | 22.34 | 0.5 | 0.62 |
| 5.5 fc1 | 100 | 45 | 1.21 | 0.13 | 67.17 | 5.45 | 37843809 | 841107 | 509 | 25439956 | 565310 | 4790 | 9 | 22.26 | 0.38 | 0.63 |
| 5.5 fc2 | 100 | 45 | 1.03 | 0.16 | 66.09 | 5.30 | 37831108 | 840625 | 435 | 22716474 | 505077 | 4575 | 9 | 22.73 | 0.38 | 0.63 |
| 5.5 fc3 | 100 | 45 | 1.05 | 0.05 | 73.49 | 2.03 | 38300033 | 851112 | 411 | 28145019 | 625345 | 1806 | 10 | 23.07 | 0.38 | 0.64 |
| 5.5 fc4 | 100 | 45 | 1.12 | 0.06 | 70.79 | 2.88 | 38734466 | 860777 | 983 | 27812491 | 600916 | 1988 | 10 | 22.97 | 0.39 | 0.65 |
| 5.10 fc1 | 100 | 45 | 1.51 | 0.27 | 63.42 | 7.49 | 37378276 | 830973 | 905 | 23968518 | 532956 | 6330 | 10 | 22.31 | 0.38 | 0.63 |
| 5.10 fc2 | 100 | 45 | 1.22 | 0.11 | 71.34 | 3.4 | 38295673 | 851102 | 572 | 27736442 | 616286 | 3123 | 10 | 22.81 | 0.38 | 0.64 |
| 5.10 fc3 | 100 | 45 | 1.64 | 1.17 | 64.19 | 12.28 | 37468869 | 833308 | 49538 | 24016223 | 533692 | 11448 | 10 | 22.83 | 0.37 | 0.62 |
| 5.10 fc4 | 100 | 45 | 1.27 | 0.17 | 70.86 | 5.12 | 39727776 | 880384 | 617 | 28072099 | 622380 | 4574 | 11 | 23.73 | 0.4 | 0.66 |

POLYPHENOLIC ADDITIVES IN SEQUENCING BY SYNTHESIS

FIELD OF THE INVENTION

The invention relates to methods, compositions, devices, systems and kits as described including, without limitation, reagents and mixtures for determining the identity of nucleic acids in nucleotide sequences using, for example, sequencing by synthesis methods. In particular, the present invention contemplates the use of polyphenolic compounds, known as antioxidant additives, to improve the efficiency of Sequencing-By-Synthesis reactions. For example, gallic acid (GA) is shown herein to be one of many exemplary SBS polyphenolic additives.

BACKGROUND

Over the past 25 years, the amount of DNA sequence information that has been generated and deposited into Genbank has grown exponentially. Traditional sequencing methods (e.g., for example Sanger sequencing) are being replaced by next-generation sequencing technologies that use a form of sequencing by synthesis (SBS), wherein specially designed nucleotides and DNA polymerases are used to read the sequence of chip-bound, single-stranded DNA templates in a controlled manner. To attain high throughput, many millions of such template spots are arrayed across a sequencing chip and their sequence is independently read out and recorded.

Systems for using arrays for DNA sequencing are known (e.g., Ju et al., U.S. Pat. No. 6,664,079). However, there is a continued need for methods and compositions for increasing the accuracy and/or efficiency of sequencing nucleic acid sequences and increasing the read lengths available for automated sequencing.

SUMMARY OF THE INVENTION

The invention relates to methods, compositions, devices, systems and kits as described including, without limitation, reagents and mixtures for determining the identity of nucleic acids in nucleotide sequences using, for example, sequencing by synthesis methods. In particular, the present invention contemplates the use of polyphenolic compounds, known as antioxidant additives, to improve the efficiency of Sequencing-By-Synthesis reactions. For example, gallic acid (GA) is shown herein to be one of many exemplary SBS polyphenolic additives.

In one embodiment, the present invention contemplates the use polyphenolic compounds as antioxidant additives to the cleave reagent during the cleave step in sequencing by synthesis (SBS). Such method of application is leads to significant improvement of the sequencing performance (raw error rate thus supporting longer read length). Such effect may be due to enhanced efficacy of the cleave reaction via scavenging of radical by-products and deactivation of excess cleave reagent. Such radical by-products may build up in the flow cell leading to carry over into the subsequent extension step thus causing premature de-protection of the 3'-OH moiety and impairing single base incorporation rate.

The present invention contemplates, in one embodiment, a method of incorporating labeled nucleotides, comprising: a) providing i) a plurality of nucleic acid primers and template molecules, ii) a polymerase, iii) a cleave reagent comprising a reducing agent and a polyphenolic compound, and iv) a plurality of nucleotide analogues wherein at least a portion of said nucleotide analogues is labeled with a label attached through a cleavable linker (e.g. a disulfide linker) to the base; b) hybridizing at least a portion of said primers to at least a portion of said template molecules so as to create hybridized primers; c) incorporating a first labeled nucleotide analogue with said polymerase into at least a portion of said hybridized primers so as to create extended primers comprising an incorporated labeled nucleotide analogue; d) detecting said incorporated labeled nucleotide analogue; and e) cleaving the cleavable linker of said incorporated nucleotide analogues with said cleave reagent. In one embodiment, the polyphenolic compound is selected from the group consisting of gallic acid, gentisic acid, pryocatechol, pyrogallol, hydroquinone, and/or resorcinol (or combinations thereof). In one embodiment, said reducing agent of said cleave reagent comprises TCEP (tris(2-carboxyethyl)phosphine). In one embodiment, said incorporated nucleotide analogues of step c) further comprise a removable chemical moiety capping the 3'-OH group. In one embodiment, the cleaving of step e) removes the removable chemical moiety capping the 3'-OH group. In one embodiment, the method further comprises f) incorporating a second nucleotide analogue with said polymerase into at least a portion of said extended primers.

It is not intended that the present invention be limited to the type of label. A variety of labels are contemplated. In a preferred embodiment, said label is fluorescent.

The present invention also contemplates compositions and reagents. In one embodiment, the present invention contemplates a cleave reagent comprising i) a reducing agent, and ii) a polyphenolic compound. In one embodiment, the polyphenolic compound includes, but is not limited to, gallic acid, gentisic acid, pryocatechol, pyrogallol, hydroquinone, and/or resorcinol. In one embodiment, said reducing agent is TCEP Tris(2-carboxyethyl)phosphine).

The present invention also contemplates kits, where reagents are supplied with instructions for their use. In one embodiment, the present invention contemplates a kit, comprising: i) the cleave reagent and ii) a plurality of nucleotide analogues wherein at least a portion of said nucleotide analogues is labeled with a label attached through a cleavable linker (e.g. a disulfide linker) to the base. In one embodiment, the cleave reagent comprises i) a reducing agent, and ii) a polyphenolic compound. In one embodiment, the polyphenolic compound includes, but is not limited to, gallic acid, gentisic acid, pryocatechol, pyrogallol, hydroquinone, and/or resorcinol. In one embodiment, said reducing agent is TCEP Tris(2-carboxyethyl)phosphine).

The present invention also contemplates systems, such as systems with flow cells where the flow cells are linked to sources of reagents. See e.g. U.S. Pat. No. 9,145,589, herein incorporated by reference. In one embodiment, the present invention contemplates a system comprising primers hybridized to template in solution, said solution comprising a cleave reagent, the cleave reagent comprising i) a reducing agent, and ii) a polyphenolic compound. In one embodiment, the polyphenolic compound includes, but is not limited to, gallic acid, gentisic acid, pryocatechol, pyrogallol, hydroquinone, and/or resorcinol. In one embodiment, said reducing agent is TCEP Tris(2-carboxyethyl)phosphine). In one embodiment, said hybridized primers and template are immobilized. In one embodiment, said hybridized primers and template are in a flow cell.

Definitions

To facilitate the understanding of this invention, a number of terms are defined below. Teams defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The team "about" as used herein, in the context of any of any assay measurements refers to +/−5% of a given measurement.

The term "linker" as used herein, refers to any molecule (or collection of molecules) capable of attaching a label and/or chemical moiety that is susceptible to cleavage. In one embodiment, cleavage of the linker may produce toxic radical products. For example, a linker may include, but is not limited to, a disulfide linker and/or an azide linker.

The term "attached" as used herein, refers to any interaction between a first molecule (e.g., for example, a nucleic acid) and a second molecule (e.g., for example, a label molecule). Attachment may be reversible or irreversible. Such attachment includes, but is not limited to, covalent bonding, ionic bonding, Van der Waals forces or friction, and the like.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand. Such nucleic acids may include, but are not limited to, cDNA, mRNA or other nucleic acid sequences.

The term "an isolated nucleic acid", as used herein, refers to any nucleic acid molecule that has been removed from its natural state (e.g., removed from a cell and is, in a preferred embodiment, free of other genomic nucleic acid).

In some embodiments, the present invention contemplates hybridizing nucleic acid together. This requires some degree of complementarity. As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5×SSPE (43.8 g/l NaCl, 6.9 g/l NaH2PO4.H2O and 1.85 g/l EDTA, pH adjusted to 7.4 with NaOH), 0.1% SDS, 5× Denhardt's reagent {50× Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length. is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

As used herein the tel "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., C0 t or R0 t analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "Tm" is used in reference to the "melting temperature." The melting temperature is the temperature at which a population of double-stranded nucleic acid molecules becomes half dissociated into single strands. As indicated by standard references, a simple estimate of the Tm value may be calculated by the equation: Tm=81.5+0.41 (% G+C), when a nucleic acid is in aqueous solution at 1M NaCl. Anderson et al., "Quantitative Filter Hybridization" In: Nucleic Acid Hybridization (1985). More sophisticated computations take structural, as well as sequence characteristics, into account for the calculation of Tm.

As used herein the term "stringency" is used in reference to the conditions of temperature, ionic strength, and the presence of other compounds such as organic solvents, under which nucleic acid hybridizations are conducted. "Stringency" typically occurs in a range from about Tm to about 20° C. to 25° C. below Tm. A "stringent hybridization" can be used to identify or detect identical polynucleotide sequences or to identify or detect similar or related polynucleotide sequences. For example, when fragments are employed in hybridization reactions under stringent conditions the hybridization of fragments which contain unique sequences (i.e., regions which are either non-homologous to or which contain less than about 50% homology or complementarity) are favored. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" or (more simply) "template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction. Dieffenbach C. W. and G. S. Dveksler (1995) In: PCR Primer, a Laboratory Manual, Cold Spring Harbor Press, Plainview, N.Y.

As used herein, the term "polymerase chain reaction" ("PCR") refers to the method of K. B. Mullis U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "label" or "detectable label" are used herein, to refer to any composition detectable by spectroscopic, photochemical, biochemical, immunochemical, electrical, optical or chemical means. Such labels include biotin for staining with labeled streptavidin conjugate, magnetic beads (e.g., Dynabeads®), fluorescent dyes (e.g., fluorescein, texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include, but are not limited to, U.S. Pat. Nos. 3,817,837; 3,850,752; 3,939,350; 3,996,345; 4,277,437; 4,275,149; and 4,366,241 (all herein incorporated by reference).

In a preferred embodiment, the label is typically fluorescent and is linked to the base of the nucleotide. For cytosine and thymine, the attachment is usually to the 5-position. For the other bases, a deaza derivative is created and the label is linked to a 7-position of deaza-adenine or deaza-guanine.

The labels contemplated in the present invention may be detected by many methods. For example, radiolabels may be detected using photographic film or scintillation counters, fluorescent markers may be detected using a photodetector to detect emitted light. Enzymatic labels are typically detected by providing the enzyme with a substrate and detecting, the reaction product produced by the action of the enzyme on the substrate, and calorimetric labels are detected by simply visualizing the colored label.

The term "luminescence" and/or "fluorescence", as used herein, refers to any process of emitting electromagnetic radiation (light) from an object, chemical and/or compound. Luminescence and/or fluorescence results from a system which is "relaxing" from an excited state to a lower state with a corresponding release of energy in the form of a photon. These states can be electronic, vibronic, rotational, or any combination of the three. The transition responsible for luminescence can be stimulated through the release of energy stored in the system chemically or added to the system from an external source. The external source of energy can be of a variety of types including, but not limited to, chemical, thermal, electrical, magnetic, electromagnetic, physical or any other type capable of causing a system to be excited into a state higher than the ground state. For example, a system can be excited by absorbing a photon of light, by being placed in an electrical field, or through a chemical oxidation-reduction reaction. The energy of the photons emitted during luminescence can be in a range from low-energy microwave radiation to high-energy x-ray radiation. Typically, luminescence refers to photons in the range from UV to IR radiation.

BRIEF DESCRIPTION OF THE DRAWINGS

FIG. 1 presents exemplary data showing a comparison of sequencing performance for runs containing gallic acid (addG) in Cleave solution vs Baseline runs. Sequencing parameters include average error rate, average percentage of perfect (error free) reads, phasing parameters (lead and lag).

FIG. 2 presents exemplary data showing a comparison of sequencing performance for runs containing gallic acid (addG) in Cleave solution vs Baseline runs. Sequencing included assessment of called variants (true positives —TP, false positives —FP).

FIG. 7 presents exemplary data showing a comparison of sequencing performance for runs containing addG alternatives in Cleave solution (pyrogallol, pyrocatechol, gentisic acid) vs baseline runs without any additive. Results are provided for two sample types (Clones and Gene Panel). Improvements are noted for sequencing KPIs such as error rate, percent perfect and lead/lag when addG alternatives such as pyrogallol, pyrocatechol, gentisic acid are added to Cleave.

FIG. 8 presents representative electropherograms of sequencing products after sequencing under baseline conditions (A) and with gallic acid additive in Cleave (B). Higher yield of full length product observed in case with additive (B).

FIG. 10 presents exemplary data showing a comparison of sequencing performance for runs containing baseline imaging buffer vs imaging buffer containing additives: GR 5.10: Replace baseline Imaging buffer with a single HEPES pH 7.5 buffer with Gentisic acid at final concentration of 25 mM; GR 5.4: Add Gentisic acid (25 mM) to Image B; GR 5.5: Image B buffer with Trolox removed and Gentisic acid added (25 mM).

DETAILED DESCRIPTION OF THE INVENTION

Figure 3:
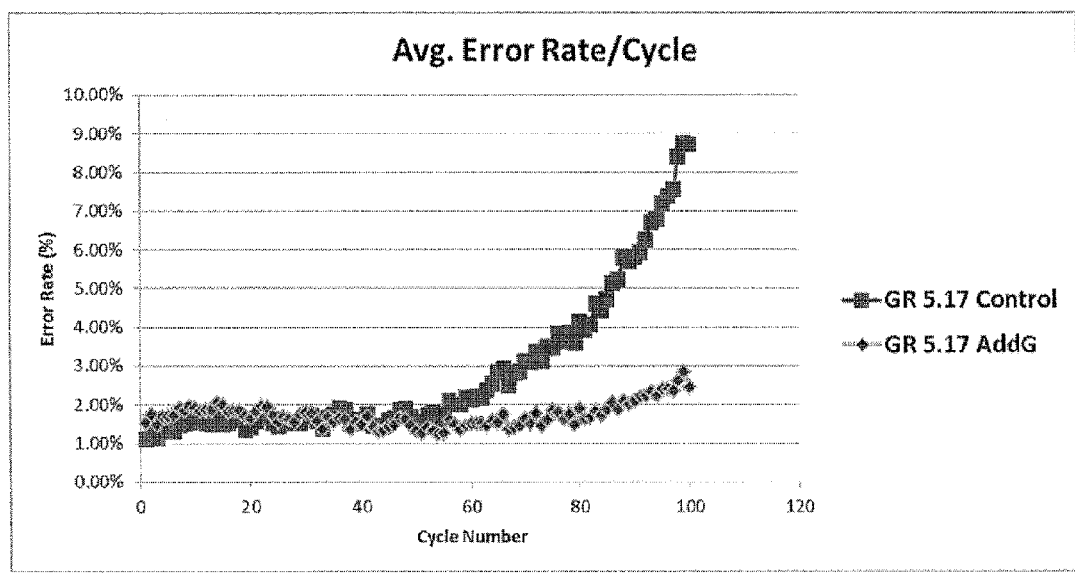
FIG. 3 presents exemplary data showing a comparison of sequencing performance for runs containing gallic acid (addG) in Cleave solution vs Baseline runs. Sequencing included assessment of average error rate per cycle.
Figure 4:
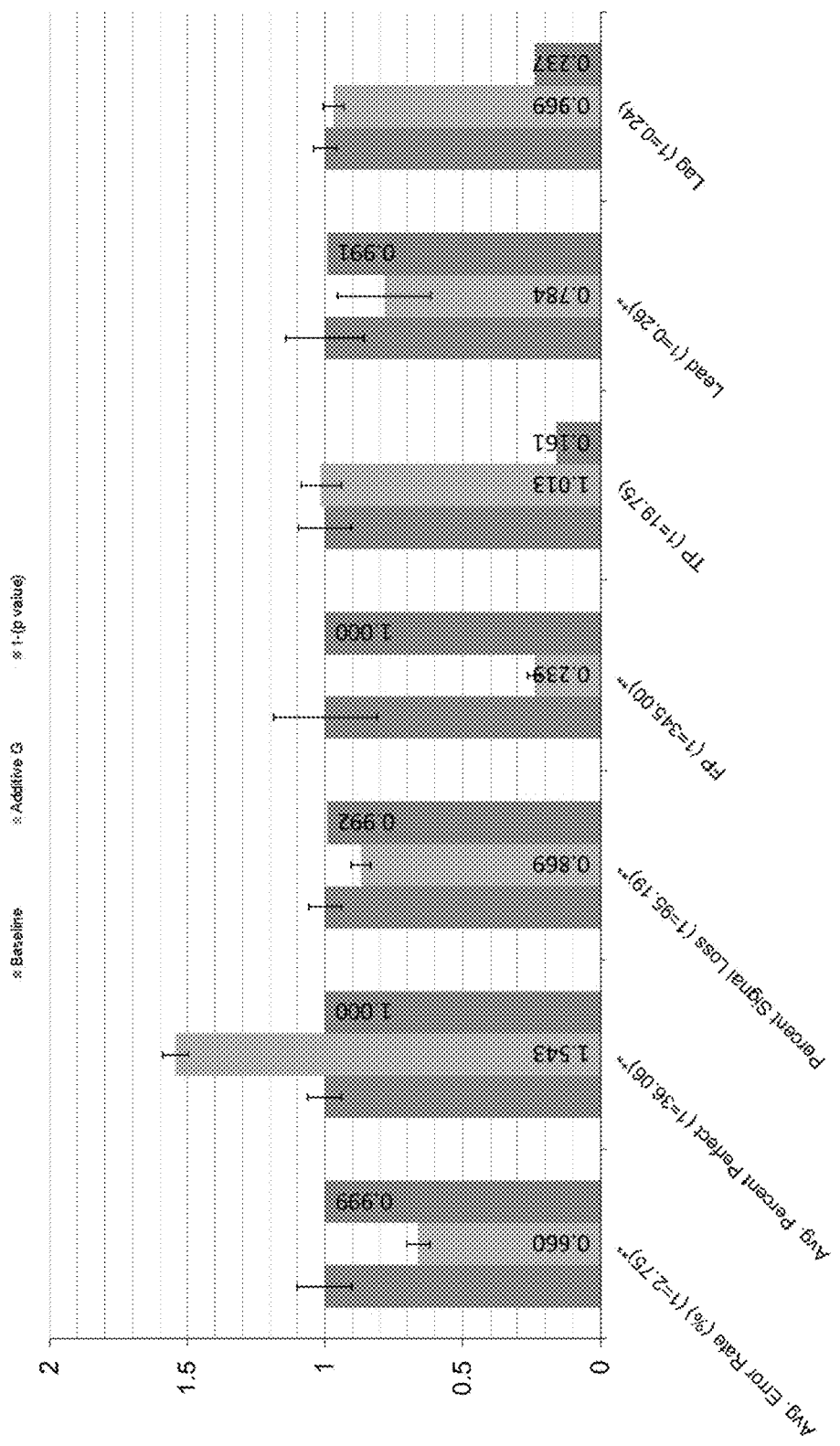
FIG. 4 presents exemplary data showing a comparison of sequencing performance for runs containing gallic acid (addG) in Cleave solution vs Baseline runs. Sequencing included assessment of the following performance indicators: average error rate per cycle, average percentage of perfect reads, percent of signal retention, false positive rate and lead/lag. Values higher than 0.95 on the third bar indicate statistical significance, first bar corresponds to baseline, second to experiment with relative improvement factor.
Figure 5:
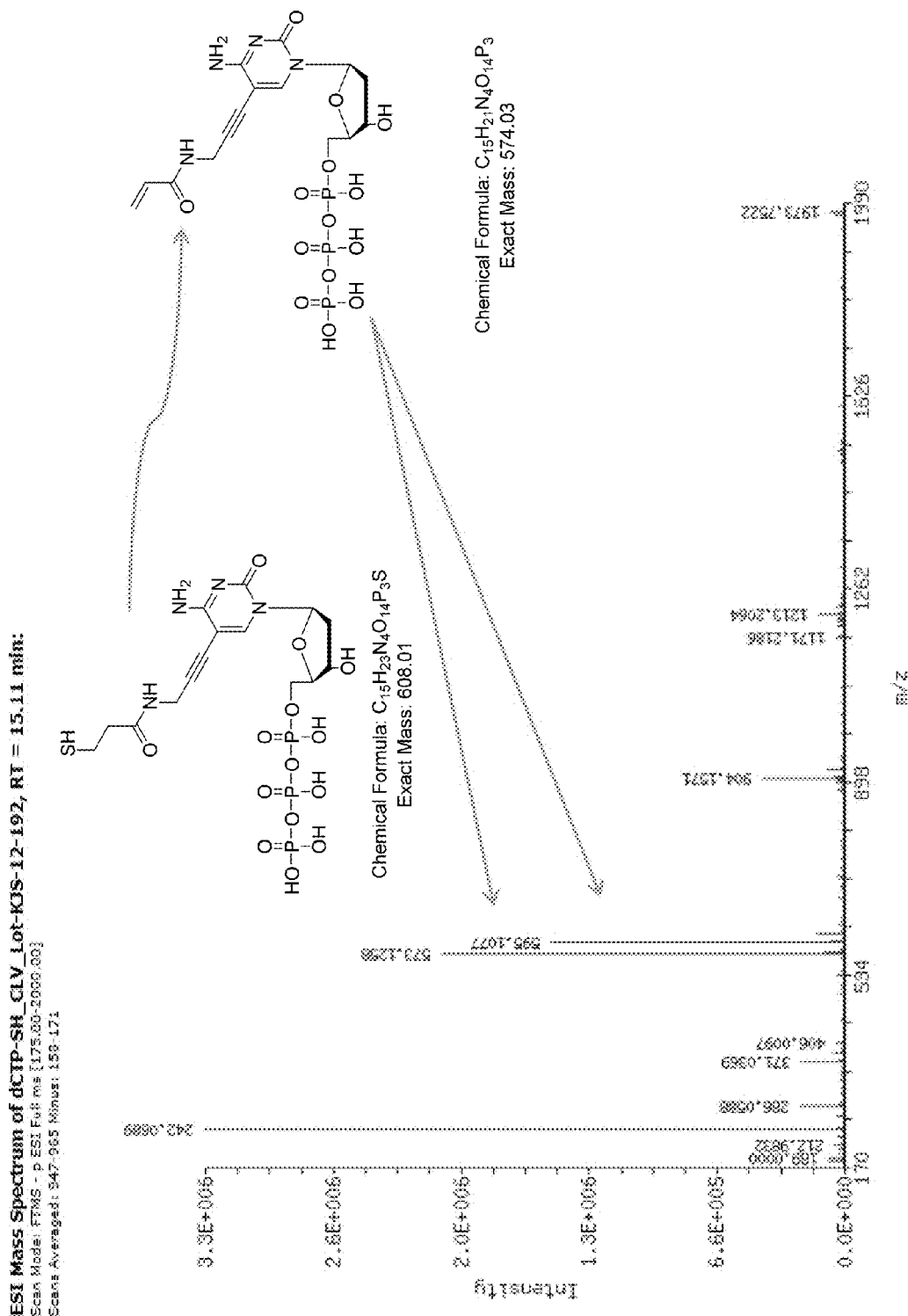
FIG. 5 presents exemplary data showing an LC-MS analysis of a cleaved spacer arm terminating with free SH group and exposure to Cleave without additives. Formation of alkene moiety detected as a result of side reactions during cleavage step.
Figure 6:
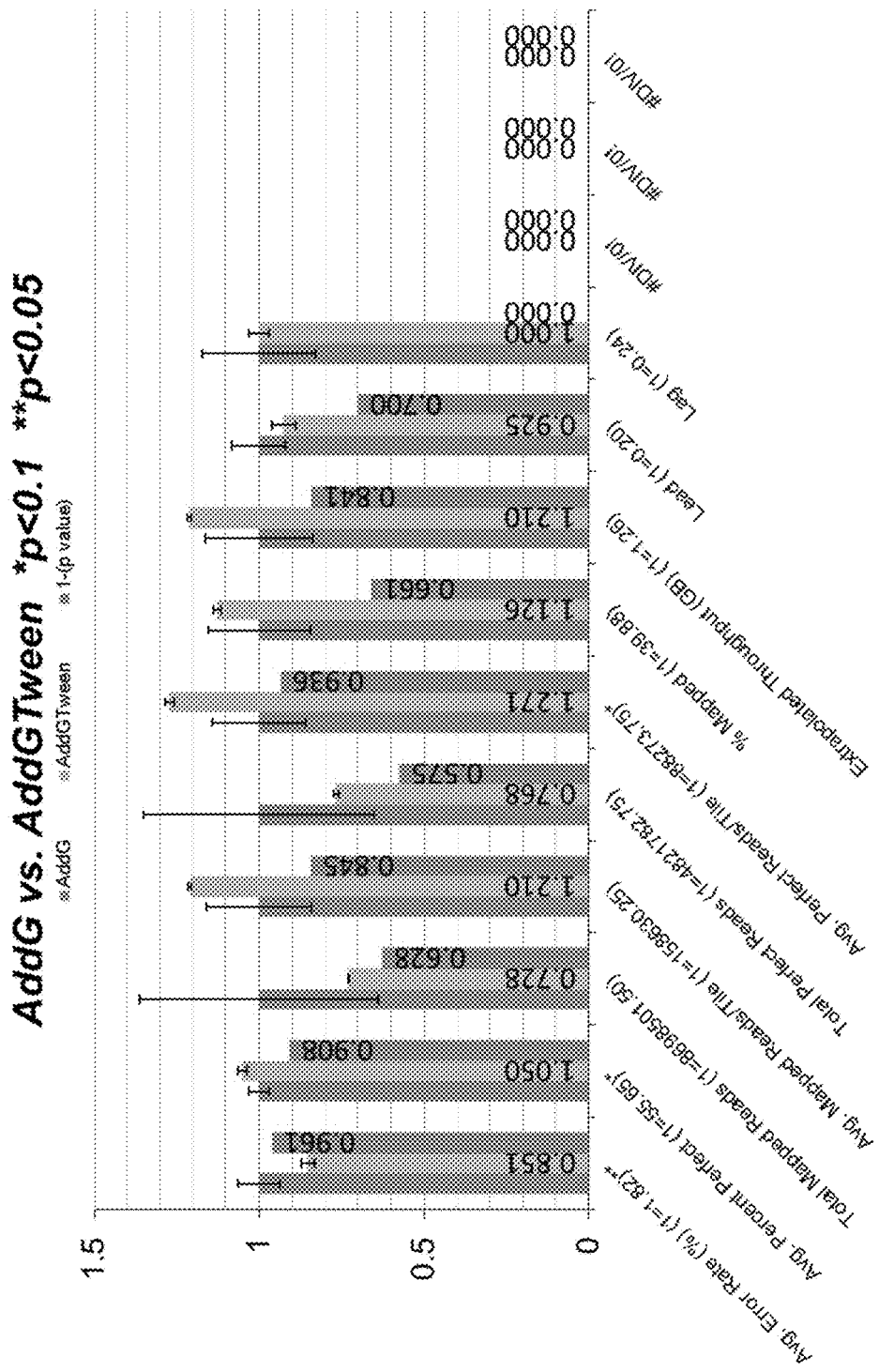
FIG. 6 presents exemplary data showing a comparison of sequencing performance for runs containing gallic acid (addG) in Cleave solution vs solutions with gallic acid and Tween detergent. Sequencing included assessment of the following performance indicators: average error rate per cycle, average percentage of perfect reads, percent of signal retention, false positive rate and lead/lag. Values higher than 0.95 on the third bar indicate statistical significance, first bar corresponds to baseline, second to experiment with relative improvement factor
Figure 9:
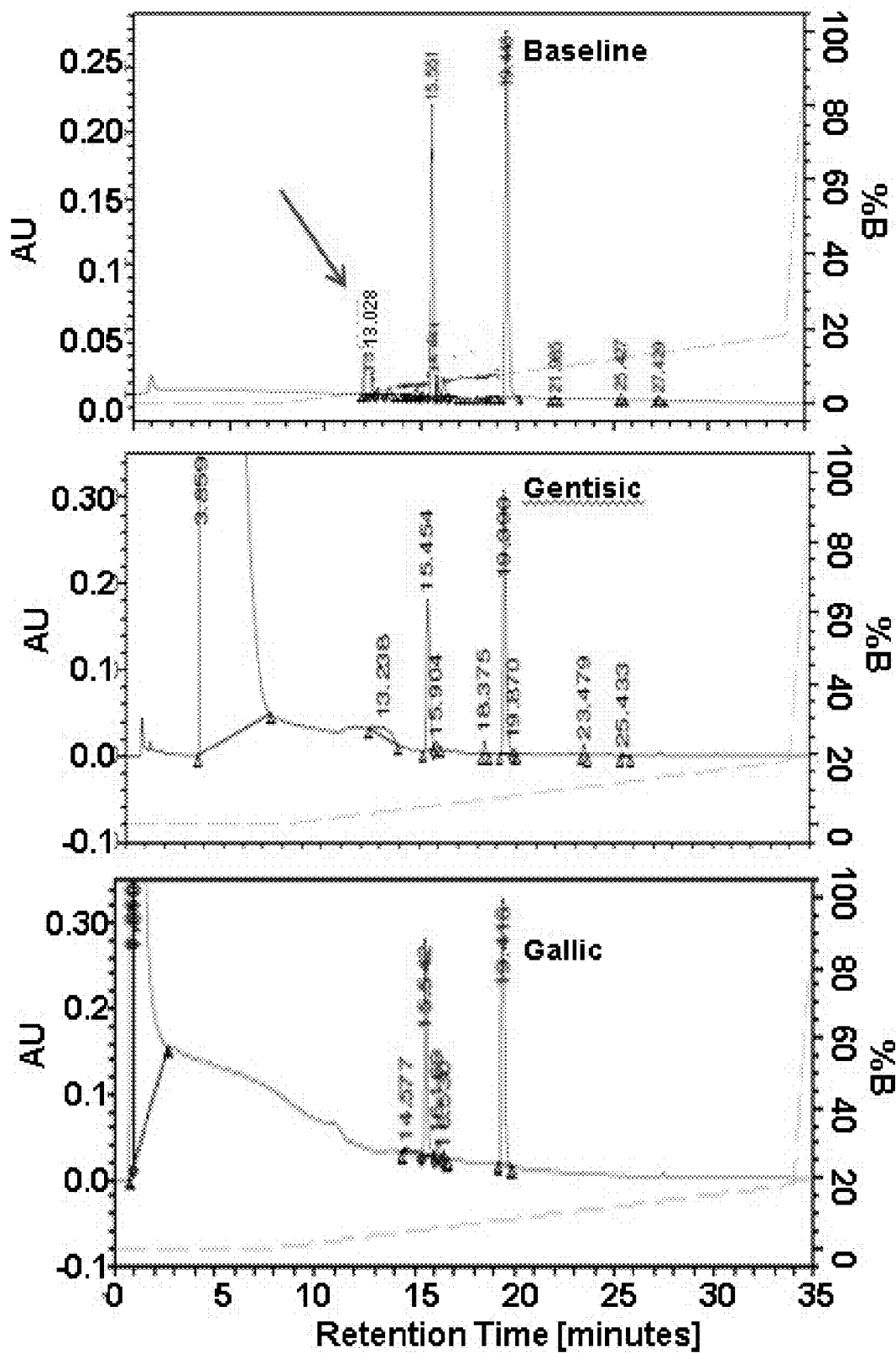
FIG. 9 presents exemplary RP-HPLC cleavage studies of labeled dCTP nucleotide in the absence (baseline) and presence of additive (examples of gallic and gentisic acid). Byproducts are clearly visible in baseline and absent in chromatograms with additives.

The invention relates to methods, compositions, devices, systems and kits as described including, without limitation, reagents and mixtures for determining the identity of nucleic acids in nucleotide sequences using, for example, sequencing by synthesis methods. In particular, the present invention contemplates the use of polyphenolic compounds, known as antioxidant additives, to improve the efficiency of Sequencing-By-Synthesis reactions. For example, gallic acid (GA) is shown herein to be one of many exemplary SBS polyphenolic additives.

I. Sequencing-By-Synthesis (SBS)

One step in the sequencing-by-synthesis workflow is the removal of the fluorescent label which is covalently attached via a cleavable linker molecule to the ring-position of the heterocyclic base of the nucleotide (reversible terminator) involved in the incorporation step. The efficacy of the cleave step is reflected not only in the efficiency of the fluorescent label cleavage but also in the mitigation of reaction by-products that could accumulate in the flow cell and interfere with subsequent base incorporation step. Examples of such compounds are radical by-products that may form due to radical pathways involved in the omolytic scission of the linker molecule to release the fluorescent label and excess cleave reagent (i. e., tris(2-carboxyethyl)phosphine or TCEP). These may build up in the flow cell and carry over into the subsequent base extension step thus causing premature de-protection of the 3'-OH moiety and causing more than one base to incorporate. An effective cleave step is important for single nucleotide incorporation throughout the sequencing reaction, as well as a prerequisite for low error rate and long read length. To improve the efficacy of the cleave step, molecules that quench radical pathways and oxidize excess TCEP are contemplated, such as ascorbic acid, so as to enhance the efficacy of this reactive step.

In one embodiment, the present invention contemplates a series of method steps performed by an automated sequencing by synthesis instrument. See U.S. Pat. No. 9,145,589, hereby incorporated by reference. In one embodiment, the instrument is comprised of numerous reagent reservoirs. Each reagent reservoir has a specific reactivity reagent dispensed within the reservoir to support the SBS process, for example:

One reactive step in a method for sequencing by synthesis using cleavable fluorescent nucleotide reversible terminators comprises cleaving a fluorescent label from a nucleotide analogue molecule. It is not intended that the present invention be limited by the nature of the cleaving agent.

In one embodiment, the SBS method comprises doing different steps at different stations. By way of example, each station is associated with a particular step. While not limited to particular formulations, some examples for these steps and the associated reagents are shown below:

1) Extend A Reagent: Comprises reversibly terminated labeled nucleotides and polymerase. The composition of Extend A is as follows:

| Component | Conc |
| --- | --- |
| PNSE (% wt/vol) | 0.005% |
| Tris × HCl (pH 8.8), mM | 50 |
| NaCl (mM) | 50 |
| EDTA (mM) | 1 |
| MgSO4 (mM) | 10 |
| Cystamine (mM) | 1 |
| Glycerol (% wt/vol) | 0.01% |
| Therminator IX* (U/ml) | 10 |
| N3-dCTP (µM) | 3.83 |
| N3-dTTP (µM) | 3.61 |
| N3-dATP (µM) | 4.03 |
| N3-dGTP (µM) | 0.4 |
| Alexa488-dCTP (nM) | 550 |
| R6G-dUTP (nM) | 35 |
| ROX-dATP (nM) | 221 |
| Cy5-dGTP (nM) | 66 |

*with Alkylated free Cysteine

2) Extend B Reagent: Comprises reversibly terminated unlabeled nucleotides and polymerase, but lacks labeled nucleotide analogues. The composition of Extend B is as follows:

| Component | Conc |
| --- | --- |
| PNSE (% wt/vol) | 0.005% |
| Tris × HCl (pH 8.8), mM | 50 |
| NaCl (mM) | 50 |
| EDTA (mM) | 1 |
| MgSO4 (mM) | 10 |
| Glycerol (% wt/vol) | 0.01% |
| Therminator IX* (U/ml) | 10 |
| N3-dCTP (µM) | 21 |
| N3-dTTP (µM) | 17 |
| N3-dATP (µM) | 21 |
| N3-dGTP (µM) | 2 |

*Alkylated free Cysteine

3) Wash solution 1 with a detergent (e.g., polysorbate 20) citrate buffer (e.g., saline)
4) Cleave Reagent: A cleaving solution composition is as follows:

| Component | Conc |
| --- | --- |
| NaOH (mM) | 237.5 |
| TrisHCl (pH 8.0) (mM) | 237.5 |
| TCEP (mM) | 50 |

5) Wash solution 2 with a detergent (e.g., polysorbate 20) a tris(hydroxymethyl)-aminomethane (Tris) buffer.

II. Polyphenolic Sequencing Additives

In one embodiment, the present invention contemplates compositions and compounds that are polyphenolic compounds as antioxidant additives which improve methods of sequencing by synthesis. In one embodiment, the polyphenolic compound includes, but is not limited to, gallic acid, gentisic acid, pryocatechol, pyrogallol, hydroquinone, and/or resorcinol.

One embodiment of the invention includes addition of polyphenolic additives in sequencing reactions of Cleavage solution to improve lifetime of solution, to reduce undesirable free radical driven side reactions, allow premixing, and as a result improve sequencing performance. Another embodiment includes addition of polyphenolic compounds to Imaging solution to improve lifetime of solution and to reduce undesirable free radical driven side reactions.

Yet another embodiment of the invention is addition of polyphenolic compounds to Extend solution to improve lifetime of solution and to reduce undesirable free radical driven side reactions. In one embodiment of the invention the polyphenolic compounds are antioxidants. In yet another embodiment the polyphenolic compounds have free radical scavenging properties.

Current sequencing processes includes a Cleave solution with buffered phosphine to deprotect 3'-OH groups and disulfide dye linker. This solution has limited activity window due to oxygen absorption from the air and open Cleave container on GeneReader instrument. Literature reports indicate that phosphines such as TCEP (Tris(carboxyethyl) phosphine) can lead to by-products with thiol-based compounds. One example is conversion of cysteine to dehydroalanine residues in peptides. The process is thought to involve a free radical path. Zhouxi et al., Rapid Commun Mass Spectrom. (2010) 24(3):267-275. Analysis of SBS nucleotides cleavage reactions in solution by means of LC-MS indicates formation of additional species in addition to expected products. Analysis of sequencing products by means of denaturing capillary electrophoresis indicates presence of non-full length products.

One Imaging solution currently used on GeneReader uses an active oxygen scavenging system and radical/triplet state scavenger. Extend A/B solutions do not contain reducing agents due to compatibility with sequencing chemistry (disufide bridges). In another embodiment, polyphenolic anti-oxidant compounds are identified that actively scavenge dissolved oxygen out of a Cleave solution and prolong useful life time of a Cleave solution and increase its efficiency. In another embodiment, improved performance of a Cleave step and reduction of side reactions is disclosed.

Preliminary data included tests with polyphenolic additives to a Cleave reagent to assess improvements SBS performance. The results suggested that several polyphenolic compounds had a high antioxidant potential. For example, two promising polyphenolic compounds were chosen for further studies: gallic acid and gentisic acid. In addition to reducing available oxygen and having positive impact on the lifetime of a Cleave solution (reducing agent) these two polyphenolic compounds had additional positive impact on sequencing performance possibly due to reducing side reactions.

Sequencing SBS chemistry performance was assessed using standard baseline SBS conditions (50 mM TCEP at pH=8.5) versus runs with additives at the same pH. To this effect, the following conclusions were made based on experimental data and described further in detail:

1. Analysis of cleavage reactions at nucleotide level by means of analytical HPLC and LC-MS (labeled and terminating nucleotide) in the absence and presence of additives was performed. These analyses revealed that cleavage reactions containing antioxidant compounds (50 mM) including, but not limited to, gallic acid, gentisic acid, pyrocatechol or pyrogallol revealed fewer side products.
2. Sequencing runs containing Cleave solution with phosphine only or containing gallic acid, gentisic acid, pyrocatechol, pyrogallol were conducted at varying concentrations. Analysis of sequencing KPIs indicates better performance as indicated by lower error rate, higher signal margin and lower lead values as well as lower false positive rate for variants effectively extending usable read length by 25-50%. Analysis by CE reveals higher yield of full length sequencing products. Flowcell data homegeneity was also improved indicating possibly beneficial impact on Cleave solution clearance from the flowcell.
3. Sequencing runs containing gallic acid, gentisic acid, pyrocatechol, or pyrogallol in Imaging solution indicated better performance as shown by lower error rate, higher signal margin and lower lead values as well as lower false positive rate for variants Analysis by CE reveals higher yield of full length sequencing products.
4. Identification of additional compounds with similar properties were identified. Additional compunds evalauted as Cleave additives showed similar benefits as demonstrated in 1-3 above. These compounds contain poly-phenolic groups or have antioxidant properties. Compounds tested include pyrogallol, pyrocatechol, hydroquinone, resorcinol, but it is not intended that the invention is limited to this set of compounds.

A. Gallic Acid

Gallic acid (GA) has been shown to improve sequencing performance and allow the system to provide a filtered trimmed sequence output of 1 Gb.

Gallic acid is found in a number of land plants, such as the parasitic plant, Cynomorium coccineum, the aquatic plant, Myriophyllum spicatum, and the blue-green alga, Microcystis aeruginosa. Zucca et al., "Evaluation of Antioxidant Potential of "Maltese Mushroom" (*Cynomorium coccineum*) by Means of Multiple Chemical and Biological Assays" Nutrients 5(1):149-161; and Nakai, S (2000). "Myriophyllum spicatum-released allelopathic polyphenols inhibiting growth of blue-green algae Microcystis aeruginosa" Water Research 34(11):3026-3032. Gallic acid is a trihydroxybenzoic acid, a type of phenolic acid, a type of organic acid, also known as 3,4,5-trihydroxybenzoic acid, found in gallnuts, sumac, witch hazel, tea leaves, oak bark, and other plants. The chemical fonnula is $C_6H_2(OH)_3COOH$, having the following structure:

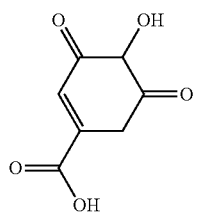 [SMILES: O=C(O)C1=CC(=O)C(O)C(=O)C1]

Gallic acid is found both free and as part of hydrolyzable tannins The gallic acid groups are usually bonded to form dimers such as ellagic acid. Hydrolysable tannins break down on hydrolysis to give gallic acid and glucose or ellagic acid and glucose, known as gallotannins and ellagitannins respectively. Gallic acid may also form intermolecular esters (depsides) such as digallic and trigallic acid, and cyclic ether-esters (depsidones) and is commonly used in the pharmaceutical industry. Fiuza et al., "Phenolic acid derivatives with potential anticancer properties—a structure-activity relationship study. Part 1: Methyl, propyl and octyl esters of caffeic and gallic acids". Bioorganic & Medicinal Chemistry (Elsevier) 12 (13): 3581-3589. Gallic acid is easily freed from gallotannins by acidic or alkaline hydrolysis. When gallic acid is heated with concentrated sulfuric acid, rufigallol is produced by condensation. Oxidation with arsenic acid, permanganate, persulfate, or iodine yields ellagic acid, as does reaction of methyl gallate with iron(III) chloride.

Gallic acid is formed from 3-dehydroshikimate by the action of the enzyme shikimate dehydrogenase to produce 3,5-didehydroshikimate. This latter compound tautomerizes to form the redox equivalent gallic acid, where the equilibrium lies essentially entirely toward gallic acid because of the coincidentally occurring aromatization. Dewick et al., (1969) "Phenol biosynthesis in higher plants. Gallic acid". Biochemical Journal 113 (3): 537-542. Gallate dioxygenase and gallate decarboxylase are enzymes responsible for the degradation of gallic acid.

Figure 11:
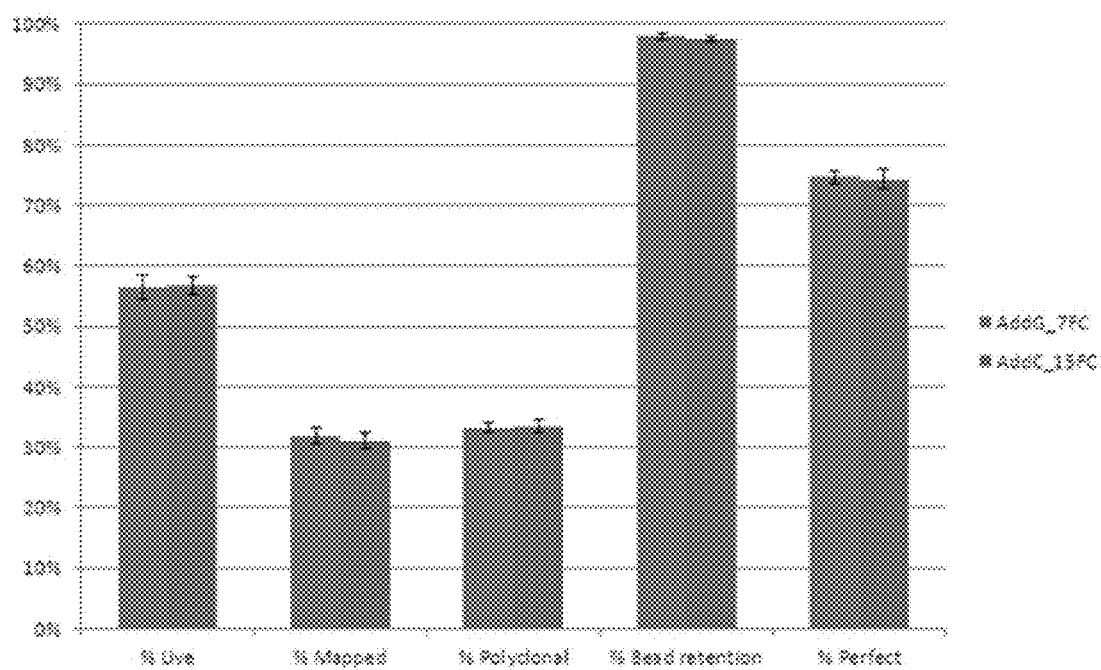
FIG. 11 presents exemplary data showing the relative bead loss in flow cells during runs comparing indole-3-propionic acid (IPA: AddC_15FC) and gallic acid (GA: AddG_7FC).

The data presented herein demonstrate that SBS runs with gallic acid showed no bead loss as shown by its comparison to SBS runs using indole-3-propionic acid (IPA). See, FIG. 11. These data show that gallic acid, like IPA, does not undergo any bead loss during SBS, contradicting previous reports. Although it is not necessary to understand the mechanism of an invention, it is believed that when a certain pH value is reached, Gallic acid undergoes an irreversible transition to a new chemical entity. It is believed that this chemical transition generates an active gallic acid derivative that is responsible for previously observed bead loss. In one embodiment, the present invention contemplates an SBS reagent (e.g., for example, a Cleave 1 buffer, where gallic acid is not mixed in the absence of TCEP. When gallic acid and TCEP are both present in the SBS reagent, no bead loss is observed.

Figure 12:
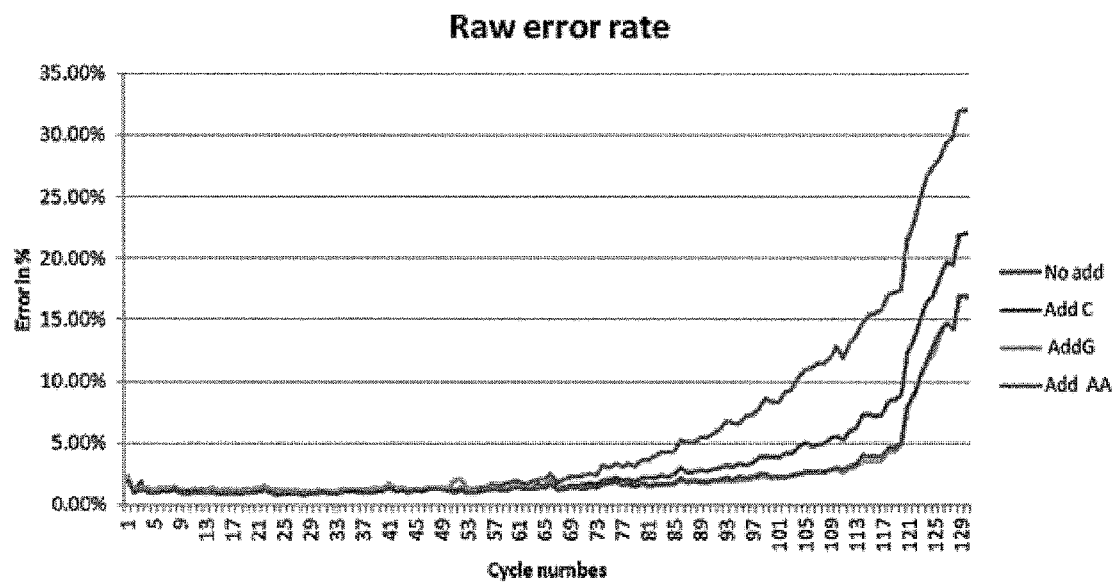
FIG. 12 presents exemplary data comparing the raw error rate for ascorbic acid (Add AA), additive C (Add C), additive G (light) along with an additive-free control (No add) where the results were generated in a sequencing run using the NA12878/101X gene panel as template. The raw error rate for ascorbic acid is significantly better than i) the no additive run, and ii) the run with additive C (while performing comparably to additive G).

This lack of bead loss is reflected in data showing improved error rates when SBS runs were compared between the presence of gallic acid, IPA and ascorbic acid. All three additives improved SBS error rates when compared to no additive. See, FIG. 12. The data show that gallic acid (AddG) results in a raw error rate that is significantly better than no additive and IPA (AddC).

B. Gentisic Acid

Gentisic acid is a dihydroxybenzoic acid. It is a derivative of benzoic acid and a minor (1%) product of the metabolic break down of aspirin. It is also found in the African tree *Alchornea cordifolia* and in wine.

Gentisic acid may be produced by carboxylation of hydroquinone:

$$C_6H_4(OH)_2 + CO_2 \rightarrow C_6H_3(CO_2H)(OH)_2$$

This conversion is an example of a Kolbe-Schmitt reaction and results in the following structure:

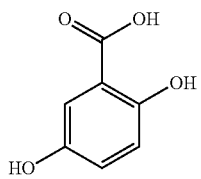

Alternatively the compound can be synthesized from Salicylic acid via Elbs persulfate oxidation (50% yield). Schock Jr. et al., (1951) "The Persulfate Oxidation of Salicylic Acid. 2,3,5-Trihydroxybenzoic Acid" The Journal of Organic Chemistry 16(11):1772-1775. As a hydroquinone, gentisic acid is readily oxidized and is used as an antioxidant excipient in some pharmaceutical preparations. In the laboratory, it is used as a sample matrix in matrix-assisted laser desorption/ionization (MALDI) mass spectrometry, and has been shown to conveniently detect peptides incorporating the boronic acid moiety by MALDI. Strupat et al., (1991) "2,5-Dihidroxybenzoic acid: a new matrix for laser desorption-ionization mass spectrometry" Int. J. Mass Spectrom. Ion Processes 72(111):89-102; and Crumpton et al., (2011) "Facile Analysis and Sequencing of Linear and Branched Peptide Boronic Acids by MALDI Mass Spectrometry" Analytical Chemistry 83(9):3548-3554.

C. Pryocatechol

Pyrocatechol, also known as catechol or 1,2-dihydroxybenzene, is an organic compound with the molecular foiiiiula $C_6H_4(OH)2$. It is the ortho isomer of the three isomeric benzenediols. This colorless compound occurs naturally in trace amounts. It was first discovered by destructive distillation of the plant extract catechin. About 20 million kg are now synthetically produced annually as a commodity organic chemical, mainly as a precursor to pesticides, flavors, and fragrances.

Catechol is produced industrially by the hydroxylation of phenol using hydrogen peroxide:

$$C_6H_5OH + H_2O_2 \rightarrow C_6H_4(OH)_2 + H_2O$$

and results in the following structure:

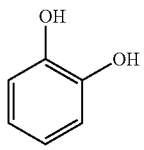

Previously, it was produced by hydrolysis of 2-substituted phenols, especially 2-chlorophenol, with hot aqueous solutions containing alkali metal hydroxides. Its methyl ether derivative, guaiacol, converts to catechol via hydrolysis of the CH3-O bond as promoted by hydriodic acid.

D. Pyrogallol

Pyrogallol is an organic compound with the formula $C_6H_3(OH)_3$ having the following chemical structure:

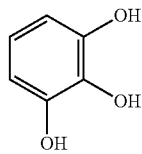

It is a white solid although because of its sensitivity toward oxygen, samples are typically brownish. It is one of three isomeric benzenetriols. It is produced by heating gallic acid that results in decarboxylation. An alternate preparation involves treating para-chlorophenoldisulphonic acid with potassium hydroxide.

E. Hydroquinone

Hydroquinone, also benzene-1,4-diol or quinol, is an aromatic organic compound that is a type of phenol, a derivative of benzene, having the chemical formula $C_6H_4(OH)_2$, having the following structure:

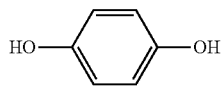

Its chemical structure features two hydroxyl groups bonded to a benzene ring in a para position. It is a white granular solid. Substituted derivatives of this parent compound are also referred to as hydroquinones.

The reactivity of hydroquinone's O—H groups resembles other phenols, being weakly acidic. The resulting conjugate base undergoes easy O-alkylation to give mono- and diethers. Similarly, hydroquinone is highly susceptible to ring substitution by Friedel-Crafts reactions such as alkylation. This reaction is exploited en route to popular antioxidants such as 2-tert-butyl-4-methoxyphenol ("BHA"). The useful dye quinizarin is produced by diacylation of hydroquinone with phthalic anhydride. Hydroquinone undergoes oxidation under mild conditions to give benzoquinone. This process can be reversed. Some naturally occurring hydroquinone derivatives exhibit this sort of reactivity, one example being coenzyme Q. Industrially this reaction is exploited both with hydroquinone itself but more often with its derivatives where one OH has been replaced by an amine.

There are various other uses associated with its reducing power. As a polymerization inhibitor, hydroquinone prevents polymerization of acrylic acid, methyl methacrylate, cyanoacrylate, and other monomers that are susceptible to radical-initiated polymerization. This application exploits the antioxidant properties of hydroquinone.

Hydroquinone can undergo mild oxidation to convert to the compound parabenzoquinone, C6H4O2, often called p-quinone or simply quinone. Reduction of quinone reverses this reaction back to hydroquinone. Some biochemical compounds in nature have this sort of hydroquinone or quinone section in their structures, such as Coenzyme Q, and can undergo similar redox interconversions.

Hydroquinone can lose an H+from both to form a diphenolate ion. The disodium diphenolate salt of hydroquinone is used as an alternating comonomer unit in the production of the polymer PEEK.

F. Resorcinol

Resorcinal is the 1,3-isomer (or meta-isomer) of benzenediol with the formula $C_6H_4(OH)_2$, having the following structure:

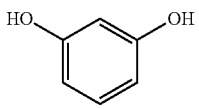

Resorcinol crystallizes from benzene as colorless needles that are readily soluble in water, alcohol, and ether, but insoluble in chloroform and carbon disulfide. Sodium amalgam reduces it to dihydroresorcin, which when heated to 150 to 160° C. with concentrated barium hydroxide solution gives γ-acetylbutyric acid and when fused with potassium hydroxide, resorcinol yields phloroglucin, pyrocatechol, and diresorcin.

EXPERIMENTAL

Example 1

In one embodiment, the present invention contemplates a SBS method comprising the steps shown in Table 1. See Olejink et al., "Methods And Compositions For Inhibiting Undesired Cleaving Of Labels" U.S. Pat. No. 8,623,598 (herein incorporated by reference in its entirety).

TABLE 1

An Exemplary SBS Workflow

| Step | Reagent | Fluid Movements | | | | |
|---|---|---|---|---|---|---|
| | | Volume mL | Speed mL/s | Station Number | Temp ° C. | Time [s] |
| 1. Dispense Reagent | Reagent 1 | 100 | 67 | 3 | 65 | 7 |
| 2. Incubate Reagent | Reagent 1 | n/a | n/a | 3 | 65 | 210 |
| 3. Dispense Reagent | Reagent 2 | 100 | 67 | 4 | 65 | 7 |
| 4. Incubate Reagent | Reagent 2 | n/a | n/a | 4 | 65 | 210 |
| 5. Dispense Reagent | Reagent 3 | 330 | 27 | 5 | Ambient | 12 |
| 6. Dispense Reagent | Reagent 4 + 5 | 200 | 27 | 5 | Ambient | 15 |
| 7. Image | n/a | n/a | n/a | 11 | Ambient | 210 |
| 8. Dispense Reagent | Reagent 3 | 330 | 27 | 20 | 65 | 12 |
| 9. Dispense Reagent | Reagent 6 | 100 | 67 | 1 | 65 | 7 |
| 10. Incubate Reagent | Reagent 6 | n/a | n/a | 1 | 65 | 210 |
| 11. Incubate Reagent | Reagent 6 | n/a | n/a | 2 | 65 | 210 |
| 12. Dispense Reagent | Reagent 7 | 990 | 27 | 2 | 65 | 37 |
| 13. Go to Step 1 | | | | | | |

Reagent 1 = Extend A;
Reagent 2 = Extend B;
Reagent 3 = Wash;
Reagent 4 = Image A;
Reagent 5 = Image B;
Reagent 6 = Cleave;
and Reagent 7 = Wash 11

All publications and patents mentioned in the above specification are herein incorporated by reference. Various modifications and variations of the described methods and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A method of incorporating labeled nucleotides, comprising:
 a) providing
  i) a plurality of nucleic acid primers and template molecules,
  ii) a polymerase,
  iii) a cleave reagent comprising a reducing agent and the polyphenolic compound gallic acid, and
  iv) a plurality of nucleotide analogues wherein at least a portion of said nucleotide analogues is labeled with a label attached through a cleavable disulfide linker to the base;
 b) hybridizing at least a portion of said primers to at least a portion of said template molecules so as to create hybridized primers;
 c) incorporating a first labeled nucleotide analogue with said polymerase into at least a portion of said hybridized primers so as to create extended primers comprising an incorporated labeled nucleotide analogue;
 d) detecting said incorporated labeled nucleotide analogue; and
 e) cleaving the cleavable linker of said incorporated nucleotide analogues with said cleave reagent.

2. The method of claim 1, wherein said reducing agent of said cleave reagent comprises TCEP (tris(2-carboxyethyl) phosphine).

3. The method of claim 1, wherein said incorporated nucleotide analogues of step c) further comprise a removable chemical moiety capping the 3'-OH group.

4. The method of claim 2, wherein the cleaving of step e) removes the removable chemical moiety capping the 3'-OH group.

5. The method of claim 4, wherein the method further comprises:
 f) incorporating a second nucleotide analogue with said polymerase into at least a portion of said extended primers.

6. The method of claim 1, wherein said label is fluorescent.

7. A kit, comprising i) a cleave reagent comprising i) a reducing agent, ii) a polyphenolic compound selected from the group consisting of gallic acid, gentisic acid, pryocatechol, and pyrogallol and iii) a plurality of nucleotide analogues wherein at least a portion of said nucleotide analogues is labeled with a label attached through a cleavable disulfide linker to the base.

8. A system comprising primers hybridized to template in solution, said solution comprising a cleave reagent comprising i) a reducing agent, and ii) a polyphenolic compound selected from the group consisting of gallic acid, gentisic acid, pryocatechol, and pyrogallol.

9. The system of claim 8, wherein said hybridized primers and template are immobilized.

10. The system of claim 8, wherein said hybridized primers and template are in a flow cell.

* * * * *